United States Patent [19]

Tu

[11] Patent Number: 4,457,747
[45] Date of Patent: Jul. 3, 1984

[54] EXCHANGE TRANSFUSION MACHINE

[76] Inventor: Ho C. Tu, 241 NE. 199th La., North Miami Beach, Fla. 33179

[21] Appl. No.: 379,064

[22] Filed: May 17, 1982

Related U.S. Application Data

[63] Continuation-in-part of Ser. No. 145,316, May 30, 1980, abandoned.

[51] Int. Cl.³ .............................................. A61M 5/00
[52] U.S. Cl. ......................................... 604/4; 604/7; 604/236; 417/538
[58] Field of Search ....................... 604/4, 5, 7, 30, 33, 604/155, 236; 417/437, 538

[56] References Cited

U.S. PATENT DOCUMENTS

| | | | |
|---|---|---|---|
| 1,531,698 | 3/1925 | Janes | 417/437 |
| 1,845,479 | 2/1932 | Carpenter | 418/45 |
| 2,093,344 | 9/1937 | Wandel | 417/538 |
| 2,625,932 | 1/1953 | Salisbury | 604/7 |
| 2,625,933 | 1/1953 | Salisbury | 604/7 |
| 2,689,565 | 9/1954 | Gobel | 604/34 |
| 2,842,124 | 7/1958 | James | 417/437 |
| 3,450,134 | 6/1969 | Willgerodt | 604/4 |

*Primary Examiner*—Stephen C. Pellegrino
*Attorney, Agent, or Firm*—Jack E. Dominik

[57] ABSTRACT

Disclosed is an exchange transfusion device with two coupled, automatically driven syringes, one in a blood withdrawal system and one in a fresh blood injection system; the coupling insuring that the volume of blood removed from a baby in the withdrawal system will be simultaneously replaced by an equal volume of fresh blood from the injection system. This simultaneous equivolumetric withdrawal and injection overcomes the physiological problems arising from the non-simultaneity of equal volumes of withdrawal and injection. The syringes in the withdrawal and injection phase of an exchange transfusion are driven at a slow steady rate, but on the refill and discard phase are driven at a high rate to avoid clotting of standing blood in the withdrawal and injection systems.

1 Claim, 3 Drawing Figures

EXCHANGE TRANSFUSION MACHINE

CROSS-REFERENCE TO RELATED APPLICATIONS

This application is a continuation-in-part of application Ser. No. 145,316, filed May 30, 1980, now abandoned.

BACKGROUND OF THE INVENTION

1. Field of the Invention.

The invention relates to blood exchange transfusions in humans. And more particularly, to device for exchange transfusions in newly born babies or children.

2. Description of the Prior Art.

The conventional method of performing exchange transfusions in newly born babies is as follows: A doctor sits close to the baby and manipulates a syringe which is connected to a three-way stop cock, the three stop cock connections being (1) the baby's umbilical arterial or venous line, (2) a source of fresh blood, and (3) a container for the waste blood. The doctor first sets the stop cock to the umbilical arterial or venous line and withdraws ten to twenty cc of blood from the baby into the syringe; the stop cock is then adjusted to the waste container line and the blood in the syringe is forced into the waste container. Next the stop cock is adjusted to the fresh blood source line and the syringe is filled with ten to twenty cc of fresh blood; and then the stop cock is adjusted to the umbilical arterial or venous line and the fresh blood forced into the baby. The cycle of withdrawal, discard, reload, and injection may be repeated as necessary. This conventional method has led to many reported complications, including the following: (1) the withdrawal of ten to twenty cc of blood from a baby results in a hypovolemic condition, which may severely effect the circulation and perfusion of the vital organs; (2) the injection of ten to twenty cc of blood into the baby may result in a hypervolemic condition; (3) by withdrawal and injection at different times, the blood pressure of the baby may go up and down following each cycle, and sudden changes in blood pressure is dangerous and could aggravate the risk of developing intracranial bleeding, especially in very premature babies; (4) withdrawal of blood from the umbilical arterial line is in accord with the physiologic flow, however the injection of fresh blood into the umbilical arterial line is contra to the physiologic flow and may disturb the circulation, giving rise to harmful effects; (5) the withdrawal and injection of blood puts the baby under severe stress, especially for the heart and may be the cause of cardiac arrest; and (6) even if an umbilical venous line is used in lieu of the umbilical arterial line, sudden change of blood pressure could interfere with the portal circulation and lead to development of necrotizing enterocolitis.

The prior art also contains devices for a continuous pumping of blood from a human through a dialyzer and back into the human. U.S. Pat. No. 2,689,565 to Gobel discloses such a device employing two syringes in a parallel push-pull arrangement so as to maintain an approximately constant blood flow by means of one-way valves.

The prior art also contains a device employing two microinfusion roller pumps, one pump for withdrawing blood and the second pump for infusing fresh blood. A problem with such roller pumps is the variation between pumps of the volume being pumped, variations as much as 6% have been noted. Such a variation would be clinically significant.

SUMMARY

This invention provides two coupled syringes, one for use in a blood withdrawal system and one for use in a fresh blood injection system; the coupling insuring that the volume of blood removed from a baby in the withdrawal system will be simultaneously replaced by an equal volume of fresh blood from the injection system. This simultaneous equivolumetric withdrawal and injection overcomes the prior art problems arising from the non-simultaneity of equal volumes of withdrawal and injection.

DESCRIPTION OF THE PREFERRED EMBODIMENTS

Figure 1:
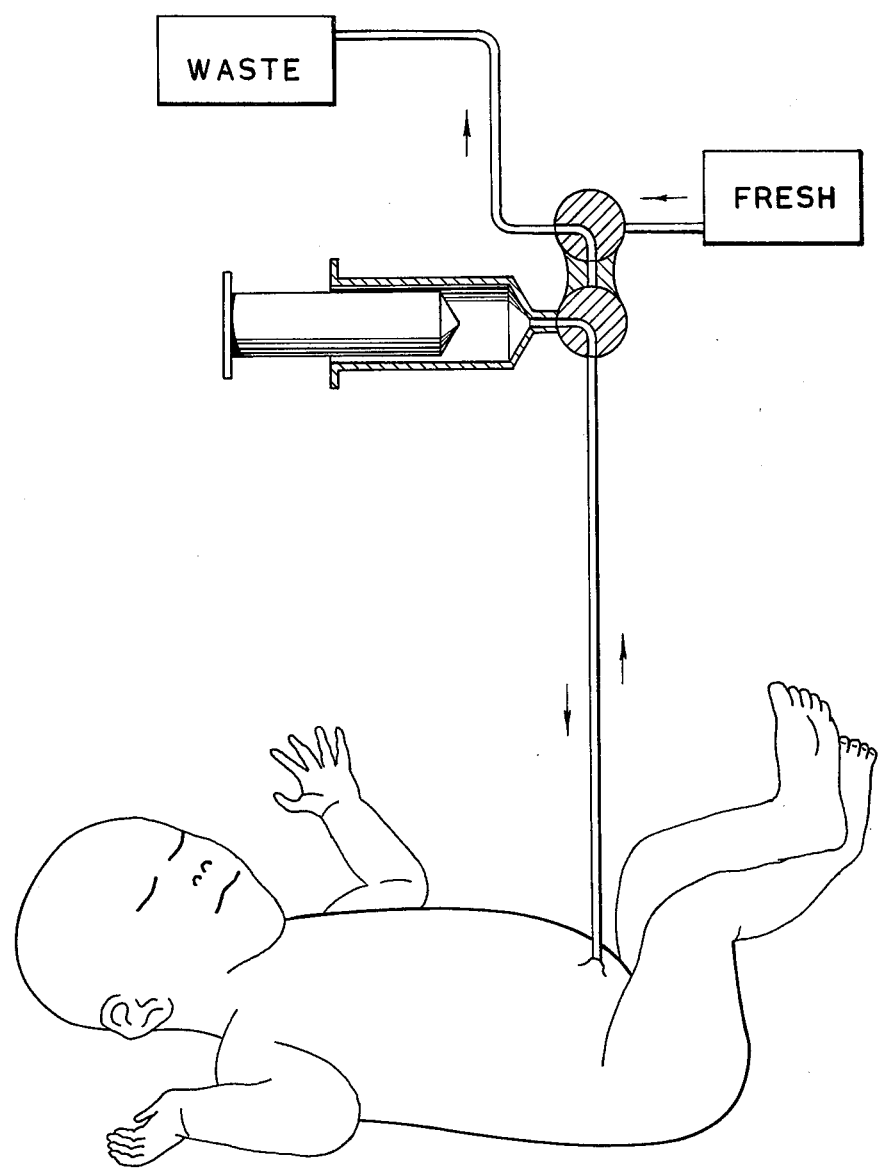
FIG. 1 illustrates the prior-art conventional method of transfusion.
Figure 2:
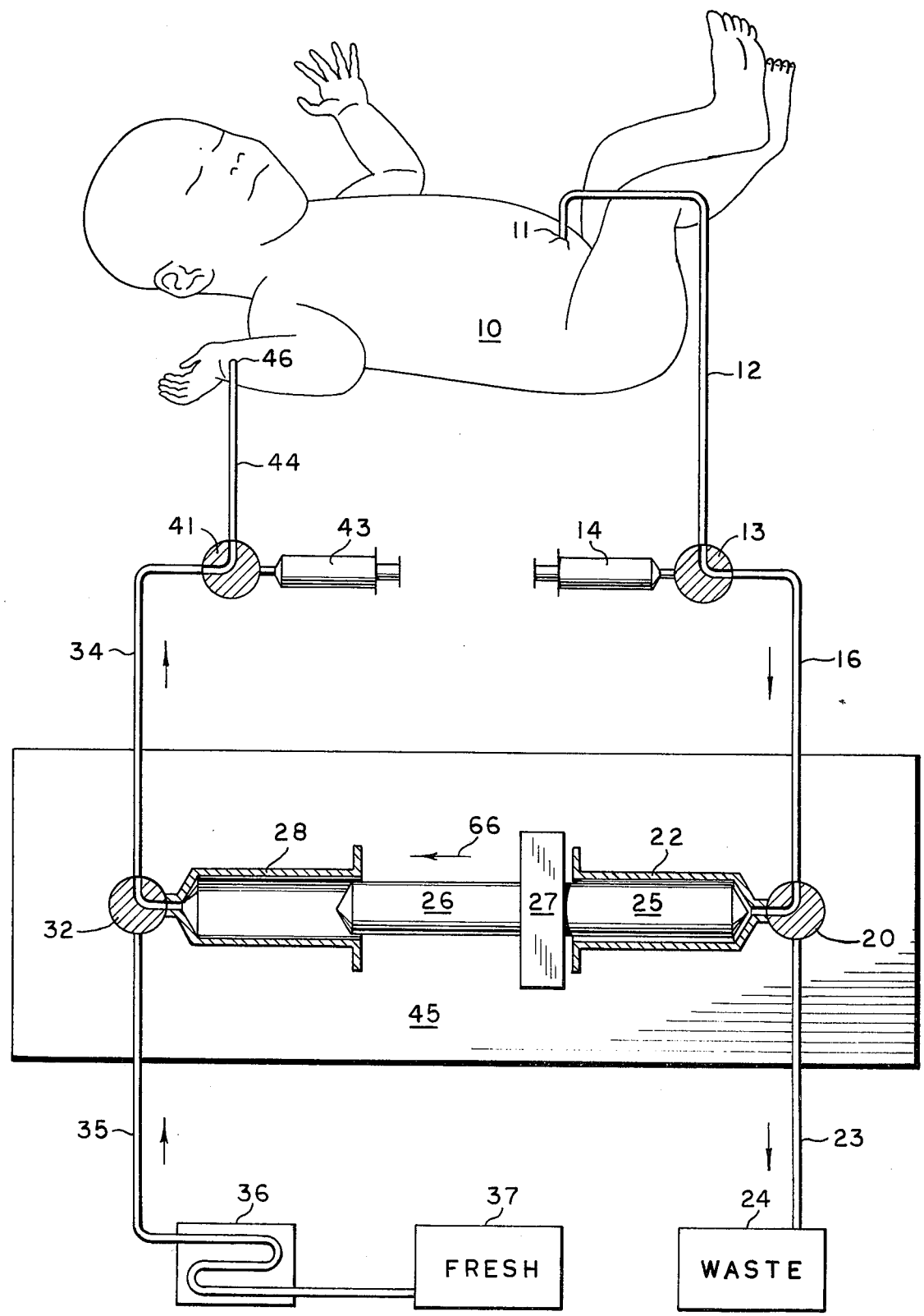
FIG. 2 diagrammatically illustrates the inventive method being used with the inventive machine.

The preferred embodiment is illustrated in FIG. 2. Baby 10 has catheter 12 (also called umbilical arterial line 12) inserted into the umbilical artery with the catheter tip 11 located at the level of the diaphragm or between $L_3$ to $L_4$. Catheter 12 (umbilical arterial line 12) is connected to stop cock 13 which in turn is connected to syringe 14 and line 16. Line 16 is connected to stop cock 20, which is also connected to syringe 22 and line 23. Line 23 empties into waste blood container 24. Syringe 22 contains syringe piston 25 which is connected to syringe piston 26 by coupler 27 so that movement of piston 25 in syringe 22 results in complementary movement of piston 26 in syringe 28. Syringe 28 is connected to stop cock 32, which in turn is also connected to line 34 and line 35. Line 35 passes through a heater 36 for warming blood and is connected to fresh blood container 37. Line 34 connects to stop cock 41 which is also connected to syringe 43 and peripheral intravenous line 44. Line 44 connects to a peripheral vein in baby 10; a connection to a vein in the wrist is illustrated in FIG. 2, although line 44 may be connected to an umbilical vein. The syringes 22 and 28 are mounted on a panel of box 45, which box contains an electric motor for driving coupled syringe pistons 25 and 26. A model 2681 Harvard volumetric infusion pump may be modified to accommodate syringes 22 and 28 of 50 cc size and provide the driving force.

Prior to use, syringes 14 and 43 are used to flush lines 12 and 44 with heparinated saline. Each cycle of exchange transfusion has two phases:

1. Withdrawal Phase.

Prior to starting the exchange transfusion, line 16, line 23, and syringe 22 are empty, and syringe 28, line 34, line 35 and line 44 are filled with fresh blood. The cycle is begun by activating the motor in box 45 to withdraw syringe piston 25 from syringe 22 and simultaneously depress syringes piston 26 into syringe 28. Blood from the baby is drawn into syringe 22 via lines 16 and 12 as syringe piston 25 is withdrawn. Stop cock 13 having been set so that syringe 14 is disconnected from the lines, and stop cock 20 having been set so that line 23 is disconnected. Blood in syringe 28 is forced through lines 34 and 44 into the peripheral vein 46 of baby 10;

stop cock 41 having been set to disconnect syringe 43 from the lines, and stop cock 32 having been set to disconnect line 35. The motor in box 45 continues the withdrawal of syringe piston 25 from syringe 22 and the depression of syringe piston 26 into syringe 28, preferably at the rate of about 75 cc to 100 cc per kilogram of baby weight per hour, depending upon the size of the baby, the smaller the baby the lower rate to be used, until syringe 28 is empty and syringe 22 is full with blood drawn from baby 10.

2. Refill Phase.

Stop cock 20 is adjusted so that syringe 22 is connected to line 23, and stop cock 32 is adjusted so that syringe 28 is connected to line 35; so upon withdrawal of syringe piston 26 from the syringe 28 and depression of syringe piston 25 into syringe 22, fresh blood from container 37 is drawn through line 35, warmed in heater 36, and into syringe 28 while simultaneously the blood withdrawn from baby 10 into syringe 22 is now forced from syringe 22 through line 23 into waste blood container 24. This refilling of syringe 28 and emptying of syringe 22 is preferably accomplished in less than a minute so that the blood in line 16 and line 12 will not have time to clot. If so, lines 12 and 44 may not need to be flushed; otherwise, these lines need to be flushed with heparinated saline by syringes 14 and 43 during this refill phase. And upon the complete depression of syringe piston 25 in syringe 22 and the corresponding maximum withdrawal of syringe piston 26 from syringe 28, the stop cocks 13 and 41 are adjusted so that syringes 14 and 43 are disconnected from lines 12 and 16 and lines 34 and 44, respectively. The cycle is ready to begin again. The important point is the difference about timing between the withdrawal phase and the refill phase for each cycle of exchange transfusion. Time for withdrawal phase varies from 15 minutes to 45 minutes, while the one for the refill phase should be preferably less than a minute.

The following table indicates the timing involved in use of the preferred embodiment for a baby weighing 3 kg.

| Size of syringes 22,28 | Time to fill syringe 22 | Time to fill syringe 28 |
| --- | --- | --- |
| 50 cc | 15 min | 30 sec |
| 100 cc | 30 min | 60 sec |

Preferably syringes 22 and 28 should be replaced every fifty to one hundred cc of blood exchanged and the exchange transfusion should be completed in about two hours. Vital signs of the baby should be done every thirty minutes. Routine lab work should be done before and after the exchange transfusion, including CBC, PT, PTT, plate, calcium, glucose, and bilirubin. Constant monitoring of the system is necessary, and the peripheral vein must be checked every ten to fifteen minutes for infiltration. If there is infiltration, the exchange should be stopped and changed to a new intravenous line.

to make certain that the rapid injection (100 cc/kg/hour) of blood through a small gauge needle such as the connection of line 44 to peripheral vein 46 would not cause undue hemolysis, blood was infused at rates of 50, 200 and 280 cc/hour through a twenty-five gauge "butterfly" needle were performed and did not result in any significant changes in the serum potassium or hematocrit of the blood after it passes through the needle.

The preferred embodiment was clinically tested on fifteen infants who required exchange transfusions because of hyperbilirubinemia. These infants were retrospectively compared to a similar group of infants chosen at random who underwent an exchange transfusion by the conventional method. Three of the infants were in both groups, having had exchange transfusions using both the preferred embodiment and the conventional method. A description of the two groups of infants and a summary of the results are presented in the following table; the superiority of the preferred embodiment is clear;

| | Preferred embodiment | Conventional method |
| --- | --- | --- |
| Gestation (weeks) | 35.8 ± 1.1 | 36.7 ± 1.0 |
| Birth weight (kg) | 2.59 ± 0.26 | 2.63 ± 0.26 |
| Pre-exchange bilirubin (mg/dl) | 17.3 ± 0.9 | 18.8 ± 0.9 |
| Post-exchange bilirubin (mg/dl) | 8.9 ± 0.3 | 11.8 ± 0.7 |
| Percent decrease in serum bilirubin | 47.5 ± 2.2 | 37.1 ± 2.2 |

Figure 3:
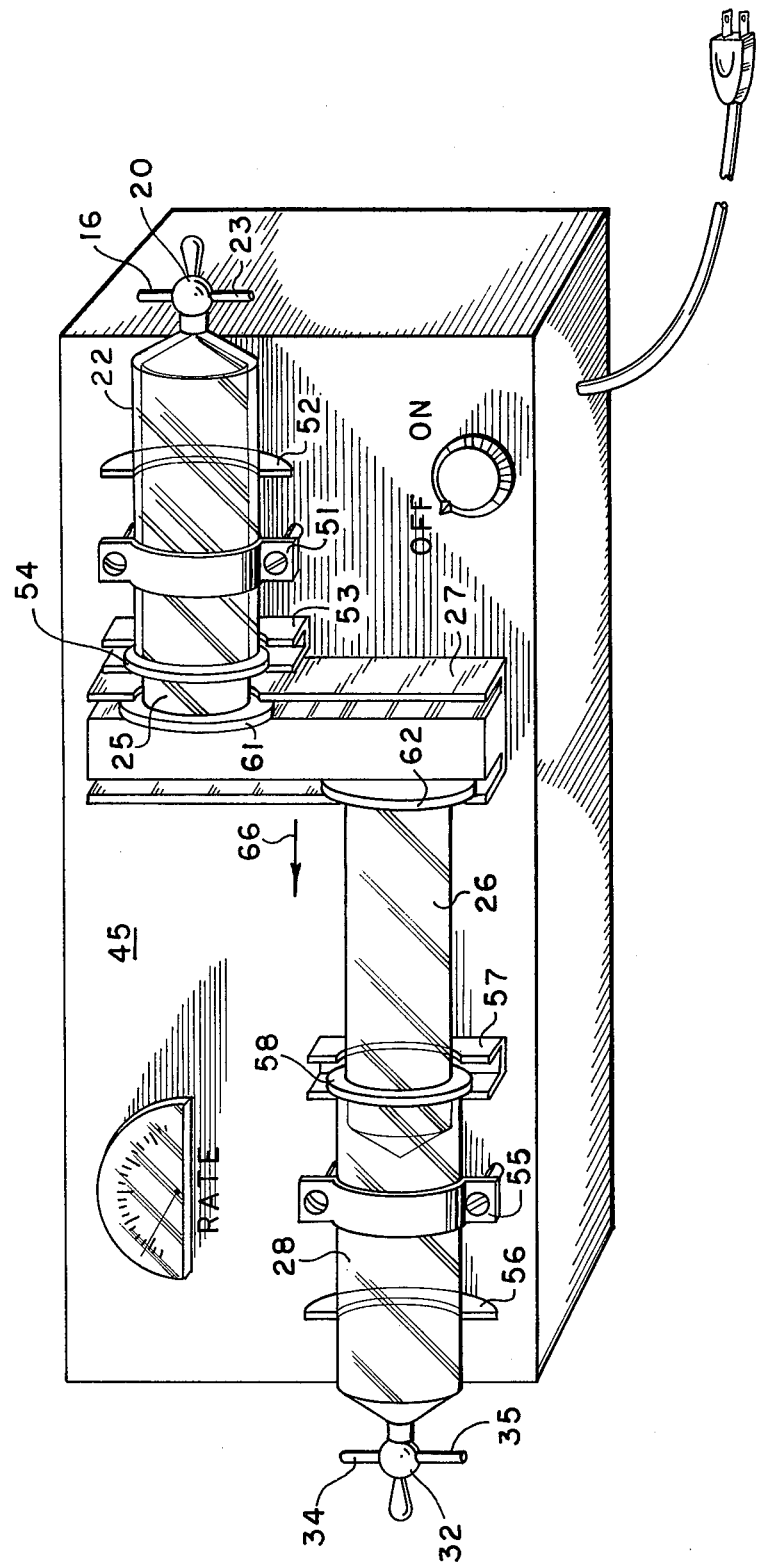
FIG. 3 shows the exterior of the inventive machine.

Referring now to FIG. 3, syringe 22 is held against the front panel of box 45 by clamp 51 and spacers 52 and 53. Spacer 53 additionally engages the lip 54 of syringe 22 so as to prevent axial movement of syringe 22. Analogously syringe 28 is held in place by clamp 55 and spacers 56 and 57, spacer 57 additionally engaging lip 58 of syringe 28 to prevent axial motion of syringe 28. Coupler 27 engages lip 61 of syringe piston 25 and lip 62 of syringe piston 26 and thereby translate displacements of syringe piston 25 into equal but complementary displacements of syringe piston 26, and vice versa. An electric motor, not shown, with appropriate gears for reduction of speed of travel is located inside box 45 and is connected to coupler 27 so that upon activation of the electric motor, coupler 27 is moved in the direction of the arrow 66 as shown in FIGS. 2 and 3; this is the part of the cycle wherein blood is being exchanged. The reverse stroke, wherein syringe 28 is refilled with fresh blood and the baby's blood in syringe 22 is forced into the waste blood container 24, may be accomplished by manual movement, or by rapid reverse movement by the electric motor located in box 45, of coupler 27, syringe piston 25, and syringe piston 26 in the direction reverse to arrow 66. Clamps 51 and 55 may be removed for easy replacement of syringes 22 and 28; further the engagement by spacers 53 and 57 of the syringe lips and of coupler 27 with the syringe piston lips is a simple tongue and groove.

I claim:

1. A machine for withdrawing blood from a human and concurrently injecting into the human fresh blood from a source as replacement for the withdrawn blood, comprising:
   (a) a first syringe,
   (b) a first tubing system including:
      (1) a first line from said human to said first syringe for carrying blood,
      (2) a second line from said first syringe to a waste blood container for carrying blood, and
      (3) a first stopcock having first and second positions:

(A) said first stopcock in said first position allows said first line to carry blood but prevents said second line from carrying blood, and (B) said first stopcock in said second position prevents said first line from carrying blood but allows said second line to carry blood, (c) a second syringe, (d) a second tubing system, including:

(1) a third line from said second syringe to said human for carrying blood, (2) a fourth line from said source to said second syringe, and (3) a second stopcock having third and fourth positions:

(A) said second stopcock in said third position allows said third line to carry blood but prevents said fourth line from carrying blood, and (B) said second stopcock in said fourth position prevents said third line from carrying blood but allows said fourth line to carry blood, (e) a coupler coupling the piston of said first syringe with the piston of said second syringe and constraining the movements of said pistons in said syringes to be complementary and approximately volumetrically equal, (f) means for withdrawing the piston in said first syringe, said withdrawing means characterized by a withdrawal rate which completely withdraws the piston in 15 to 45 minutes, (g) means for depressing the piston in said first syringe, said depressing means characterized by a depression rate which completely depresses the piston in less than one minute.

* * * * *